United States Patent [19]

Mercier

[11] Patent Number: 5,363,862
[45] Date of Patent: Nov. 15, 1994

[54] DISPOSABLE SURGICAL INSTRUMENT PASSER

[76] Inventor: Charles W. Mercier, 695 Buena, Lake Forest, Ill. 60045

[21] Appl. No.: 66,506

[22] Filed: May 24, 1993

[51] Int. Cl.$^5$ .............................................. A61F 5/37
[52] U.S. Cl. ................................. 128/846; 128/878; 128/879
[58] Field of Search ............... 128/845, 846, 878, 879; 206/363, 364, 365, 366, 557, 565

[56] References Cited

U.S. PATENT DOCUMENTS

| | | | |
|---|---|---|---|
| 2,369,728 | 2/1945 | Farkas | 206/557 |
| 3,200,983 | 8/1965 | Walter | 220/22 |
| 3,208,583 | 9/1965 | Kamps | 206/557 |
| 3,504,832 | 4/1970 | Corvetti | 206/557 |
| 3,564,662 | 2/1971 | Dold | 21/84 |
| 4,011,944 | 3/1977 | Cooley et al. | 206/557 |
| 4,046,254 | 9/1977 | Kramer | 206/370 |
| 4,053,280 | 10/1977 | Salisbury | 21/87 |
| 4,216,860 | 8/1980 | Heimann | 206/565 |
| 4,305,629 | 12/1981 | Friis | 206/565 |
| 4,736,844 | 4/1988 | Scott et al. | 206/370 |
| 4,844,245 | 7/1989 | Bennett | 206/366 |
| 4,844,249 | 7/1989 | Coulombe | 206/438 |
| 4,848,570 | 7/1989 | Gosciniak | 206/366 |
| 4,889,231 | 12/1989 | Foote et al. | 206/363 |
| 4,915,918 | 4/1990 | Nichols | 422/292 |
| 4,936,449 | 6/1990 | Conard et al. | 206/366 |
| 4,974,728 | 12/1990 | Colton | 206/366 |
| 5,005,590 | 4/1991 | Eldridge, Jr. et al. | 128/849 |
| 5,020,665 | 6/1991 | Bruno | 206/366 |
| 5,024,326 | 6/1991 | Sandel et al. | 206/366 |
| 5,097,963 | 3/1992 | Chernosky et al. | 211/60.1 |
| 5,160,324 | 11/1992 | Halbach | 604/192 |
| 5,165,539 | 11/1992 | Weber et al. | 206/363 |
| 5,181,609 | 1/1993 | Spielmann et al. | 206/370 |
| 5,183,643 | 2/1993 | Nichols | 422/297 |

*Primary Examiner*—Michael A. Brown
*Attorney, Agent, or Firm*—Tilton Fallon Lungmus

[57] ABSTRACT

A disposable surgical instrument passer is disclosed for conveying surgical instruments between nurses, doctors and other medical personnel during the performance of surgical procedures and the like. The instrument passer generally comprises an elongate receptacle for receiving surgical instruments, a handle connected to the receptacle for hand-carrying the receptacle, and a flared shield positioned adjacent the handle for shielding a holder's hand from contact with the usually sharp instruments while the instruments are being placed into the receptacle and preventing possible injury and transmission of infectious disease. A disposable instrument passer and small instrument disposal container combination is also disclosed wherein the passer includes a container for permanently receiving small disposable instruments and safely containing the instruments for permanent disposal.

25 Claims, 3 Drawing Sheets

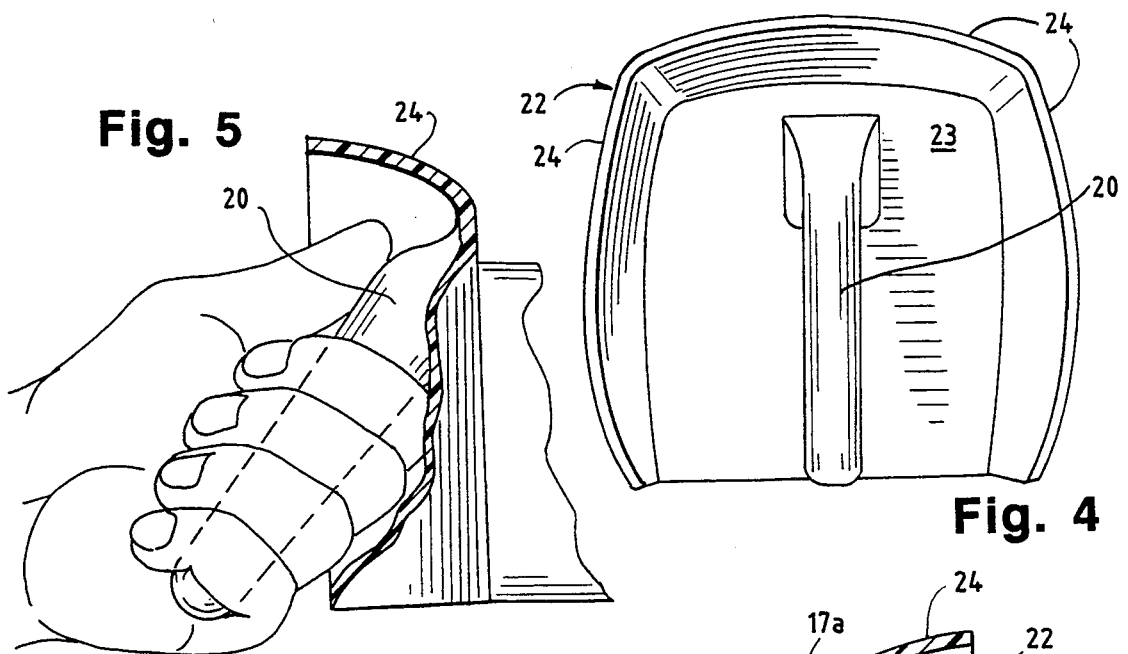
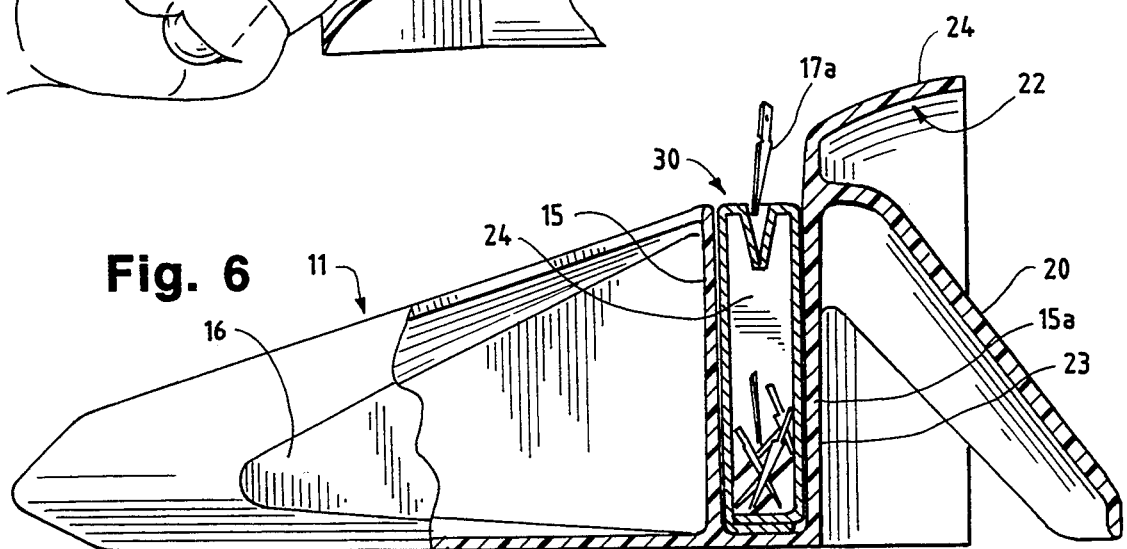
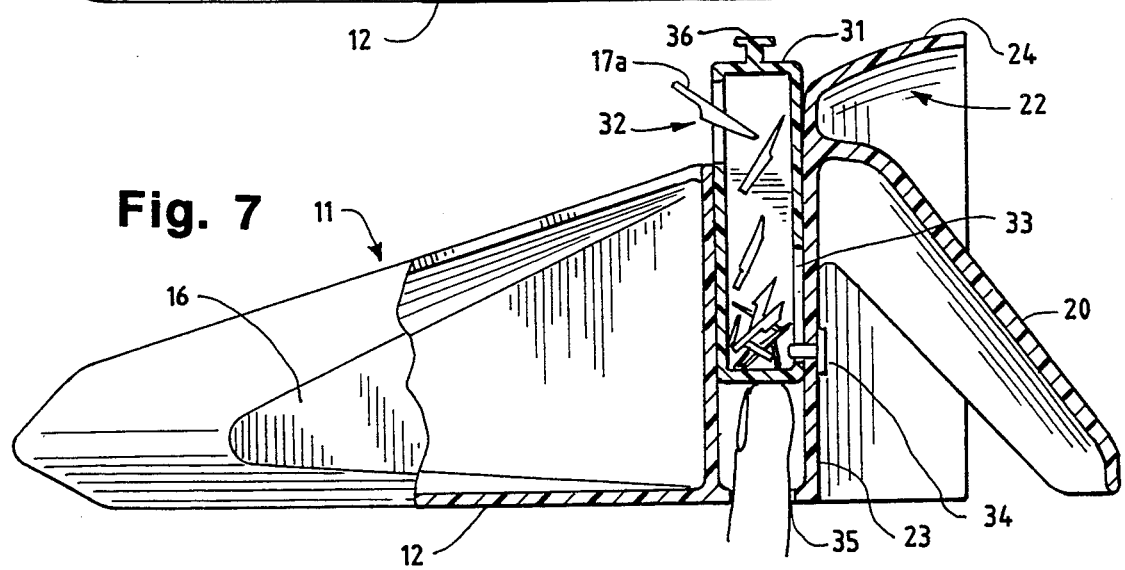

DISPOSABLE SURGICAL INSTRUMENT PASSER

BACKGROUND AND SUMMARY

The present invention relates to devices for passing medical instruments, such as scalpels, suture needles, surgical sharps, and syringes, between medical personnel during surgical procedures. More particularly, this invention relates to a disposable instrument passer for protecting a holder's hand from injury and possible transmission of infectious disease while handling medical instruments.

Many devices are known in the art for receiving medical instruments, surgical sharps, needles, and the like. These devices generally consist of trays or bins adapted to receive the sharp ends of such instruments as disclosed in U.S. Pat. Nos. 5,097,963, 5,024,326, 5,020,665, and 5,005,590. These devices all generally have open box-like structures that, while shaped to receive the sharp ends of a plurality of medical instruments, do not provide means for ensuring that a person holding the device is not injured when instruments are inserted or placed into the device. In fact, as many of these devices have open box-like structures, it is quite common for a person holding the device to allow one or more fingers to extend into the box-like area where the instruments are inserted.

These prior art devices are particularly deficient in a situation where a nurse is carrying instruments back and forth between a surgical platform, commonly known as a Mayo stand, and the surgical field. The danger occurs when the nurse holds the receptacle out for a doctor or other person to insert used instruments therein. Due to the sensitivity and urgency of certain surgical procedures, it could be quite easy for an instrument to be quickly placed, or thrust, into the receptacle with the possibility of injuring the hand of the person holding the receptacle, as the holder typically has one or more fingers in the area where the instruments are received. Perhaps more dangerous than possible nicks, cuts or scratches that can be inflicted on the holder's hand, is the possible danger of transmission of infectious diseases.

During surgery, instruments are commonly in contact with blood and other bodily fluids which can contain infectious diseases such as hepatitis or AIDS. The tragic outbreak of AIDS alone has caused people in the medical field to be particularly concerned with contracting such diseases by coming into contact with or being cut by soiled instruments. The prior art devices, wherein people typically hold the device with one or more fingers extending into the instrument receptacle area, are highly deficient in that during complicated surgical procedures it would be quite easy for an instrument to injure a person's hand with possibly disastrous consequences.

An important aspect of this invention therefore lies in providing a receptacle for receiving and conveying medical instruments during surgical procedures that protects the holder's hand from possible injury and transmission of infectious disease. Briefly, the present invention provides a receptacle for receiving surgical instruments, a connected handle for hand-carrying the receptacle, and a flared shield positioned adjacent the handle for shielding a holder's hand from contact with the instruments while they are being placed into the receptacle.

The present invention is particularly advantageous in that it can be molded in a one-piece construction of a puncture-resistant polymeric material that is inexpensive and easy to manufacture. Having such a construction, the device can be manufactured for single use and thereafter be disposable. This negates the need for sterilizing the receptacle with an autoclave or other device which is often time consuming and expensive.

In one embodiment of the present invention, the receptacle can be designed to have a generally planar bottom, a pair of vertical side walls, and a first back wall which together define a trough for receiving instruments. A second back wall can be placed between the side walls and a distance apart from and in parallel relation to the first back wall to define a disposal bin. This bin preferably has a rectangular shape and a lid can be hingedly attached to one of the side walls to seal the bin. This bin is particularly effective for receiving small instruments such as needles, surgical sharps, and suture needles for permanent disposal. Typically, such components must be permanently sealed in a puncture-resistant container prior to disposal to prevent accidents which could occur during transportation to a landfill or other permanent disposal means. Thus, the disposable instrument passer of this invention can perform the dual functions of acting as an instrument conveyor and as a permanent receptacle for small disposable instruments— thereby conserving materials, reducing manufacturing expenses, reducing overall medical expenses and further providing the environmental advantages of conserving energy and reducing waste in landfills.

Other embodiments of the present invention include modifications to the disposal bin. One such modification can take the form of placing a removable, puncture-resistant container for receiving small instruments into the bin so that the container can be replaced when full. The removable containers act as permanent disposal containers for the small instruments while the instrument passer effectively protects the holder's hand from harm. Another modification can take the form of placing a pop-up container into the bin which can be simply pushed up to receive small instruments and then pushed back into position to effectively, permanently and safely contain small disposable instruments. In another embodiment, a tray means is disposed in the bin and including retaining means for receiving the small surgical instruments, such as polystyrene strips or magnetic strips.

Other features, advantages, and objects of the invention will become apparent from the specification and drawings.

DRAWINGS

FIG. 4 is an end view of the present invention.

FIG. 5 is a partial cross-sectional view of a hand grasping the handle of the present invention.

FIG. 6 is a partial cross-sectional side view of another embodiment of the present invention.

FIG. 7 is a partial cross-sectional side view of a further embodiment of the present invention.

DETAILED DESCRIPTION OF PREFERRED EMBODIMENT

Figure 1:
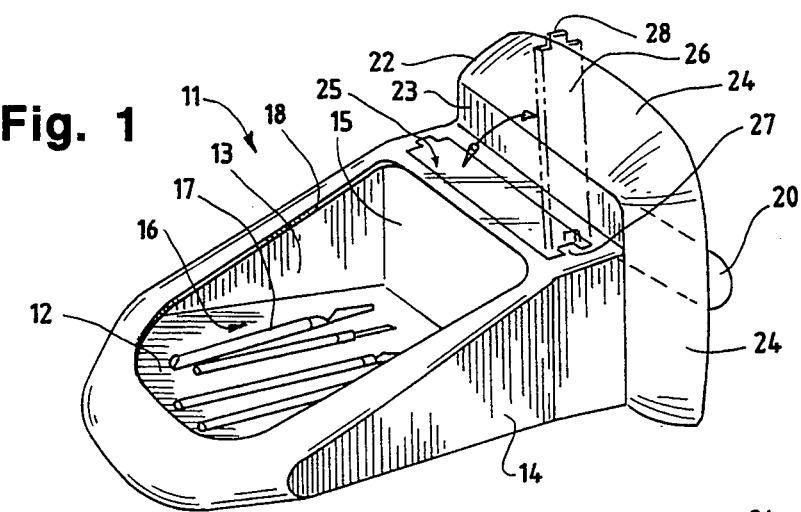
FIG. 1 is a perspective view of the disposable surgical instrument passer of the present invention.
Figure 2:
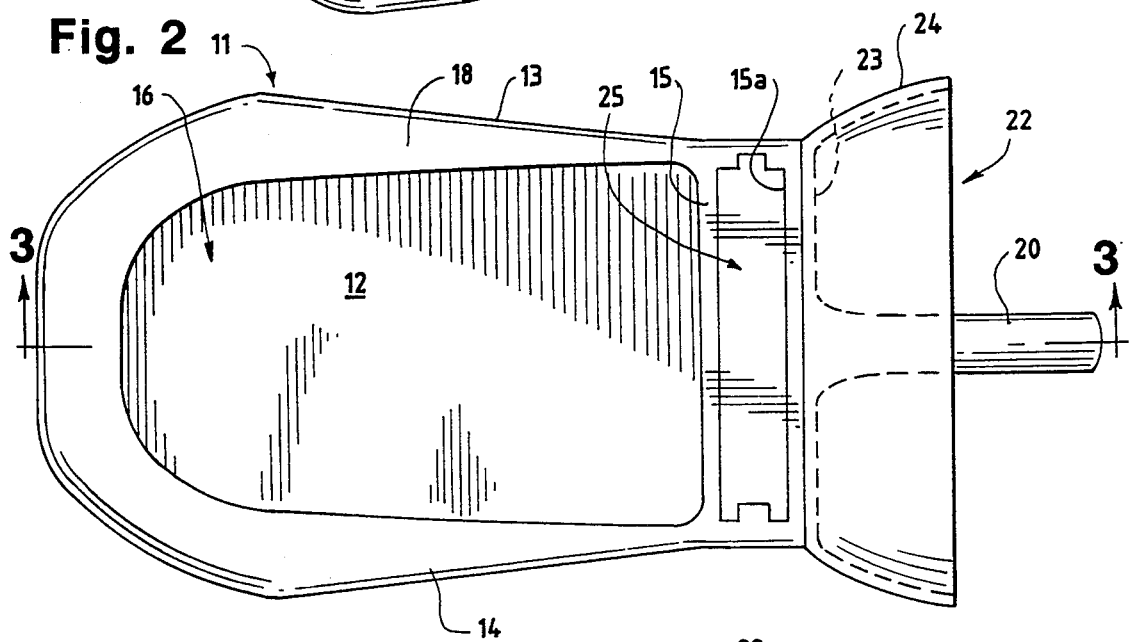
FIG. 2 is a top plan view of the present invention.

Referring to the drawings, the numeral 10 generally designates the disposable surgical instrument passer of the present invention. Passer 10 includes a receptacle means generally designated by the numeral 11 and shown in this embodiment as comprising a generally planar bottom 12, a pair of side walls 13, 14 and a back wall 15. Together, bottom 12, side walls 13, 14, and back wall 15 define an elongated trough 16 for receiving instruments 17. Preferably, side walls 13, 14 and back wall 15 have an extended lip 18 which extends a short distance over the trough to help prevent the instruments from bouncing out of the receptacle. It is contemplated that the receptacle is most advantageous for use with medical instruments, such as scalpels, syringes, suture needles and the like, however the invention is not so limited and can be used to convey or pass other instruments such as commonly used in the dental, veterinary and other similar fields.

Figure 3:
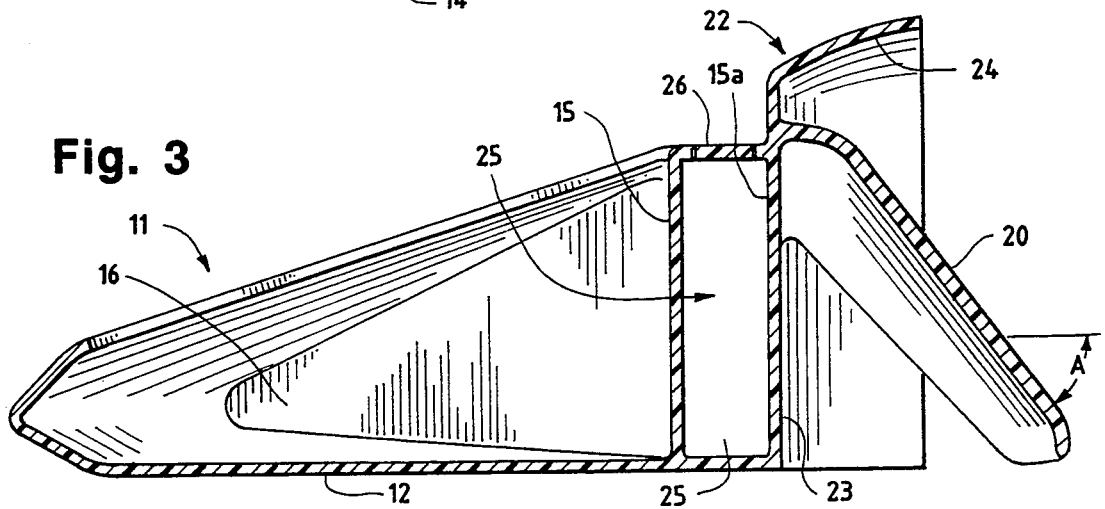
FIG. 3 is a side cross-sectional view taken along the line 3—3.

A handle means is connected to the receptacle and shown in this embodiment as a single elongate member 20. Handle 20 can be integrally molded with the receptacle means or can be adhesively attached as known in the art. Preferably, as best shown in FIGS. 3, 4 and 5, handle 20 is sloped downwards to form an angle A with a longitudinal axis of the receptacle means. Positioning handle 20 at such an angle to the receptacle causes a person grasping the handle to extend their wrist and project the entire passer outwards as shown in FIG. 5. This has the affect of positioning the holder's arm generally along the longitudinal axis of the receptacle means and thus away from the receptacle means where the instruments are received. This is contrasted to a situation wherein a handle is positioned along the longitudinal axis of the receptacle, which would cause a person's forearm to extend perpendicular to the receptacle and thus in close proximity to the receptacle where the instruments are placed. Although such an elongate, angled handle 20 is preferred, any handle means can be employed such as a U-shaped member (not shown) or any other means which facilitates handcarrying of the receptacle.

Guard means, generally designated 21, are positioned adjacent the handle means for protecting a holder's hand from inadvertent contact with the instruments while they are being placed into the receptacle. Guard means 21 in this embodiment takes the form of a flared shield 22. Shield 22 has a central plate portion 23, which may also comprise part of back wall 15, and a somewhat peripheral, extended flange 23 which projects over handle 20. Preferably, flange 23 extends from the plate portion over the top and sides of handle 20.

Flared shield 22 is preferably integrally molded with the receptacle means and handle means to form one unitary structure constructed of puncture-resistant polymeric material. Examples of such suitable materials are polyvinylchloride, polystyrene, polypropylene, or other rigid formed plastics such as nylon. Utilizing such puncture-resistant materials for receptacle 11 and shield 22 provides an effective passer for protecting a holder's hand from contact with the sharp ends of instruments while they are being placed in the receptacle. For example, in the event that an instrument being placed in the receptacle was not squarely received in trough 16, shield 22 would provide protection for the holder's hand by shielding it with puncture-resistant material. This puncture-resistant material would also prevent an instrument from cutting through to the handle area, if roughly placed or thrust into the receptacle. Furthermore, positioning handle 20 at a downward angle positions the holder's arm away from the receptacle, further reducing the chances of an accident occurring.

Passer 10 can preferably be constructed to include a pair of first and second back walls 15 and 15a, generally positioned in parallel relation and apart from each other to define a bin 25. Bin 25 is advantageous for receiving small instruments 17a, such as surgical sharps, needles, and the like, and permanently containing these instruments to prevent accidents during disposal. As passer 10 is generally designed to be discarded after use, the provision of such a bin for permanently disposing of such small instruments results in more efficient use of materials and thus less waste.

Bin 25 is preferably provided with a lid 26 (shown in phantom in FIG. 1) which is attached to one of the side walls 13 or 14 by a hinge 27. This lid can be provided with a releasable locking tab 28 for sealing the lid prior to permanent disposal of the entire unit.

As an alternate embodiment (shown in FIG. 6), bin 25 can be constructed as a box-shaped opening for receiving a smaller disposable box-like container 29. Container 29 is preferably constructed of puncture-resistant material and is shaped to easily slide in and out of bin 25 so that once container 29 is full, the container can easily be removed for permanent disposal and another, empty, container can then be inserted in its place. The use of such removable containers is advantageous in that the guard means, shown as shield 22, extends above the opening of the bin 25 to shield a holder's hand, grasping handle 20, from the small sharp instruments as they are being placed into the container. In this respect, bin 25 can be shaped to accommodate existing permanent disposal containers and provide the advantageous of a guard means for protecting the holder's hand.

Container 29 can also include a one-way opening 30 so that blades and the like can be inserted into the container but cannot be removed. As known in the art, opening 30 may also be constructed to facilitate removal of blades, surgical sharps or needles from their respective handles or the like. (See U.S. Pat. No. 4,844,245.)

A further embodiment is illustrated in FIG. 7 wherein a pop-up container 31 is positioned in bin 25 for receiving small instruments and for permanently containing these instruments for disposal. Pop-up container 31 preferably has an opening 32 into which small instruments and the like can be inserted for containment in container 31. Container 31 is moveable within bin 25 a certain distance which is controlled by a slot 33 and a respective pin 34, which limits the range of motion of container 31. An aperture 35 is defined by bin 25 for allowing a person to insert a finger through the aperture and push the container into an elevated position for receiving instruments. Once the finger is removed from aperture 35, container 31 slides (or can be pushed) back into bin 25, effectively containing the small instruments for disposal. Also, a tab 36 can be placed on top of the container allowing someone to pull the container up to the open portion or push the container back down to the closed position.

Figure 8:
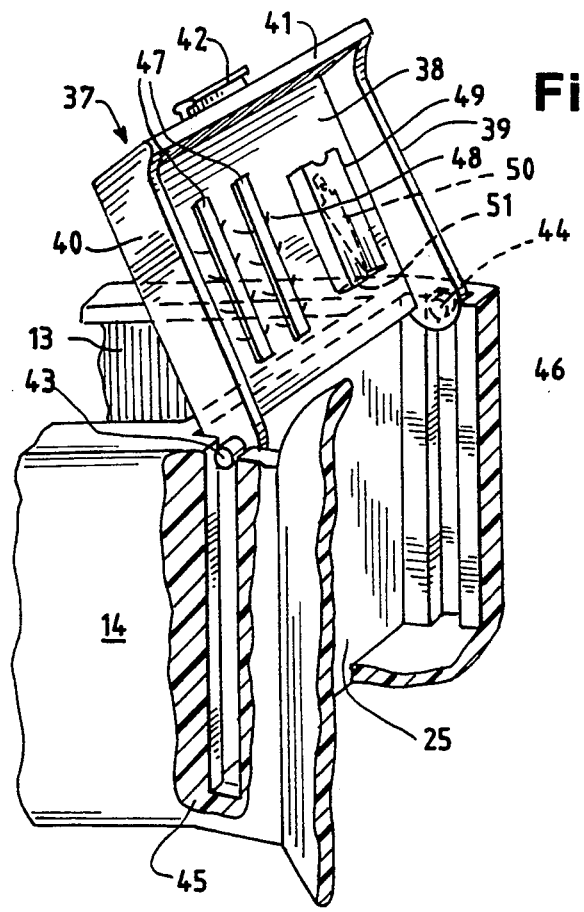
FIG. 8 is a partial cross-sectional view of a further embodiment of the present invention.
Figure 9:
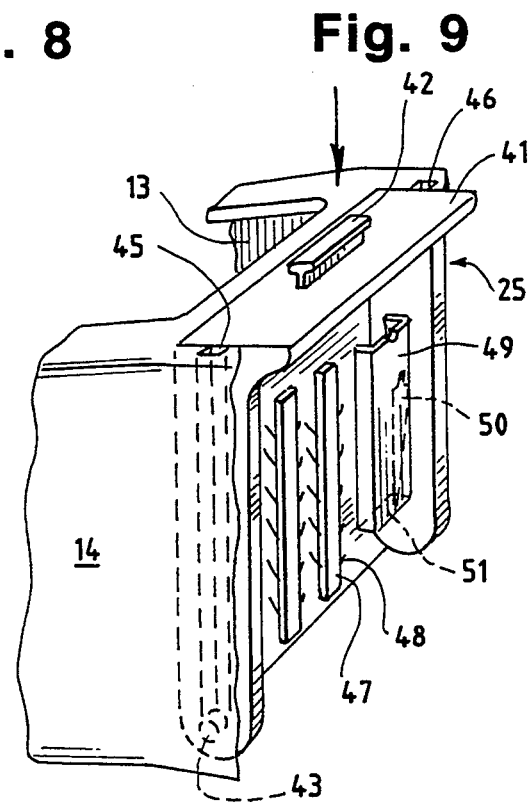
FIG. 9 is a partial cut-away perspective view of the embodiment of the invention shown in FIG. 8.
Figure 10:
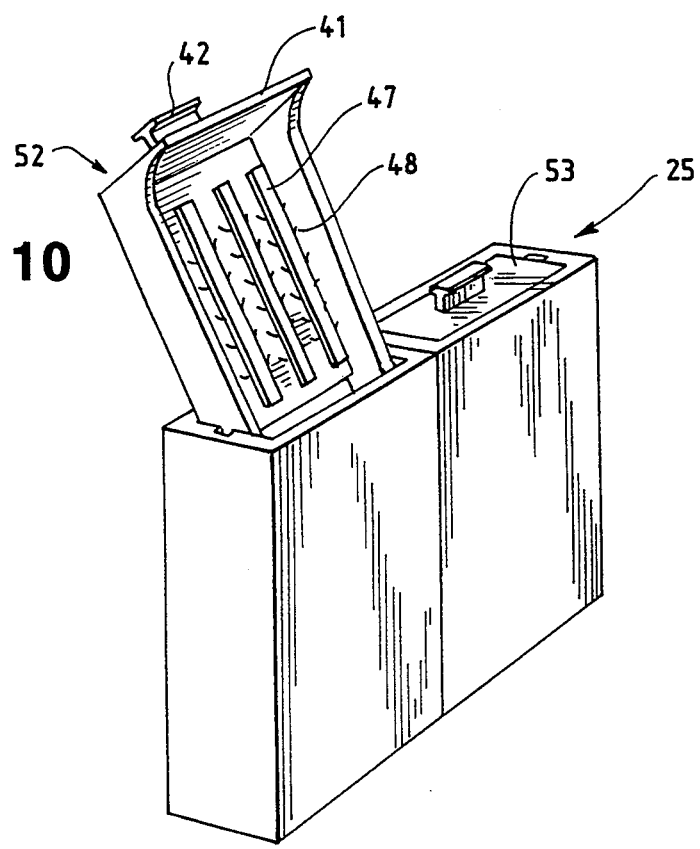
FIG. 10 is a partial perspective view further illustrating an embodiment of the present invention.

FIGS. 8, 9 and 10 illustrate further embodiments of the present invention in which a tray means is disposed in bin 25 for receiving small surgical instruments. The tray means is shown generally as tray 37 having an upright wall 38, a pair of side walls 39 and 40, and a closure lid 41. A tab 42 is disposed on closure lid 41 to facilitate sliding of tray 37 in and out of bin 25. To achieve this sliding action, side walls 39 and 40 each have respective pins 43 and 44 which are slideably received in slots 45 and 46 on side walls 13 and 14. Although tray 37 is preferably slideable on pins 43 and 44 in slots 45 and 46, it will be understood that any means for allowing tray 37 to easily slide in and out of bin 25 may be utilized.

As shown in FIG. 8, tray 37 can be pulled to an upright position and tilted backwards to expose a face of upstanding wall 38. Additionally, tray 37 can be completely removed from bin 25 and placed back in the bin after small instruments have been disposed on upright wall 38. FIG. 9 illustrates tray 37 in a completely closed condition where closure lid 41 seals the top of bin 25.

Upstanding wall 38 is shown as having a plurality of receiving means for retaining small surgical instruments thereon such as suture needles, scalpel blades and other surgical sharps. A plurality of solid strips 47 are shown for receiving insertable needles and the like securely therein. Suture needles 48 are shown as being inserted through the strips so that the strips frictionally will retain the suture needles. Although any material may be used for strips 47 which allows needles to be inserted therethrough and frictionally retained, it has been found that polystyrene is a preferable material.

Alternative receiving means can take the form of a rectangular shaped box 49 for receiving small surgical instruments, such as scalpel blades 50 (shown in phantom). One of the walls of box 49 is preferably comprised of magnetic material or includes a magnetic strip, such as magnetic strip 51 which comprises the bottom of box 49. Alternatively, any one of the other walls of box 49 can be comprised of magnetic material, or have a magnetic strip disposed thereon, or a magnetic strip can be adhesively attached to upstanding wall 38 for retaining instruments in box 49. Embodiments of other retaining means on upstanding wall 38 can include a plurality of magnetic strips for each retaining metal needles, knife blades and other surgical sharps on tray 37.

FIG. 10 illustrates that bin 25 can be split into two separate compartments each having a tray means 52 and 53, each being provided for receiving different types of instruments. For example, tray 52 can be provided with strips 47 for receiving suture needles 48 and tray 53 can be provided with magnetic strips for receiving other medical instruments. Providing such removable trays allows medical personnel to safely dispose small surgical instruments on a tray means and then safely insert the tray means into the instrument passer for conveying, carrying and permanent disposal, as desired. The tray means are also particularly advantageous in that the tray can be simply lifted to examine the contents and receive an accurate count of the surgical instruments contained therein. This is important because after surgical procedures, all of the instruments used must be accounted for to ensure that no instruments have been lost or are in a place which could present a hazardous condition.

The disclosed combinations of the instrument passer and the disposal bin are greatly advantageous in conserving materials, limiting waste, ease of manufacture, and convenience of use. However, these combinations also have the further advantage that the provision of dual back walls 15 and 15a, or the provision of the removable or pop-up container, or the provision of the pull-out tray, provides assurance that a sharp instrument, such as a scalpel, cannot pass through the instrument passer to the handle area in which a holder's hand is positioned. This is particularly important when considering that the passer is constructed of puncture-resistant materials which, although effective, is not absolutely puncture-proof. Therefore, if a sharp instrument were roughly thrust into the receptacle, it is possible that the sharp edge of the instrument could pierce one of the back walls of the receptacle. However, by providing a disposal bin at the back of the receptacle having dual walls 15 and 15a, or a removable or pop-up container or tray, the chances of an instrument passing through to the handle area are extremely remote.

With the advent of such diseases as AIDS, there is a definite need in the medical field for economical safeguards that limit the possibility of contracting such deadly diseases. The instrument passer of the present invention is greatly advantageous in providing a safe and effective means for shielding a person's hand from danger while handling medical, dental or other such instruments during surgical procedures and the like. The combination of the passer and a permanent disposal container is also greatly advantageous in adding the feature of a safe container for receiving small instruments, such as surgical sharps and the like, for permanent disposal, while protecting the holder's hand from possible contact with these instruments. As the passer itself is constructed to be disposable, the additional provision of the container for permanently receiving such small instruments is greatly advantageous in that it reduces the number of objects needed in an operating room, reduces the use of materials and associated costs, and is environmentally sound in reducing the amount of materials being placed in landfills or other disposal sites.

While in the foregoing, an embodiment of the invention has been disclosed in considerable detail for purposes of illustration, it will understood by those skilled in the art that many of these details many be varied without departing from the spirit and scope of the invention.

I claim:

1. A disposable instrument passer for protecting a holder's hand from possible injury and transmission of infectious disease while handling sharp instruments, said passer comprising:
    receptacle means for receiving sharp instruments;
    handle means connected to said receptacle means for hand-carrying said receptacle means; and
    guard means positioned adjacent said handle means for shielding a holder's hand from contact with said instruments while said instruments are being placed into said receptacle means, said guard means including a shield having a plate portion positioned transverse to a longitudinal axis of said receptacle means.

2. The instrument passer of claim 1 wherein said shield is flared.

3. The instrument passer of claim 2 wherein said shield includes extended flanges which project from said plate portion over at least a portion of said handle means.

4. The instrument passer of claim 3 wherein said extended flanges are positioned to project over at least a portion of said holder's hand when said holder grasps said handle means.

5. The instrument passer of claim 2 wherein said shield has a generally concave shape towards said handle means.

6. The instrument passer of claim 1 wherein said receptacle means includes an elongated trough for receiving said instruments and is defined by a generally planar bottom, a pair of vertical side walls, and first back wall portion.

7. The instrument passer of claim 6 wherein a second back wall is positioned between said pair of side walls and in parallel relation to and spaced apart from said first back wall to define a bin having an opening.

8. The instrument passer of claim 7 wherein a hinged lid is attached to one of said side walls to releasably close said opening of said bin.

9. The instrument passer of claim 1 wherein said handle means includes an elongate handle positioned at an angle to a longitudinal axis of said receptacle means to facilitate positioning of a holder's forearm along said longitudinal axis when said holder grasps said handle.

10. The instrument passer of claim 9 wherein said angle is at least 25°.

11. The instrument passer of claim 1 wherein said receptacle means and said guard means are integrally formed of a puncture-resistant material.

12. The instrument passer of claim 1 wherein said passer is integrally constructed of puncture-resistant material.

13. A disposable instrument passer and small instrument container combination, said combination comprising:
   a receptacle defined by a generally planar bottom, a pair of vertical side walls, and a first back wall portion;
   handle means connected to said receptacle for hand-carrying said receptacle;
   container means disposed in said receptacle for receiving small disposable instruments and providing a permanent container for safely containing said small instruments for permanent disposal; and
   shield means positioned adjacent said handle means and said container means for shielding a holder's hand from contact with said instruments while said instruments are being placed into said receptacle or said container means.

14. The combination of claim 13 wherein said shield means includes a flared shield having a plate portion positioned transverse to a longitudinal axis of said receptacle and extended flanges which project from said plate portion over at least a portion of said handle means to cover at least a portion of said holder's hand when said holder grasps said handle means.

15. The combination of claim 13 wherein said container means is defined by said first back wall portion of said receptacle, a second back wall portion spaced in parallel relation and apart from said first back wall portion, said side walls connecting said first and second back walls and said bottom, said container means including a releasable but lockable lid attached to one of said side walls.

16. The combination of claim 13 wherein a second back wall portion is spaced in parallel relation and apart from said first back wall portion to form a generally rectangular box-shaped opening and said container means comprises a removable generally rectangular container disposed in said box-shaped opening.

17. The combination of claim 16 wherein said container is made of a puncture-resistant material and includes a puncture-resistant closable lid for releasably sealing said opening and opening receiving said small instruments therein.

18. The combination of claim 17 wherein said opening includes a pair of sloped walls which act as a one-way entrance to the container.

19. The combination of claim 18 wherein said walls of said one-way entrance are positioned to facilitate removal of said small instruments from a handle body such that said small instruments fall into the container.

20. The combination of claim 13 wherein a second back wall portion is spaced in parallel relation and apart from said first back wall portion to form a generally rectangular box-shaped opening and said container means comprises a pop-up slideable container having an opening which is accessible when said pop-up container is in an elevated position.

21. A disposable instrument passer and small instrument reception tray combination, said combination comprising:
   a receptacle defined by a generally planar bottom, a pair of vertical sidewalls, and a first back wall portion;
   handle means connected to said receptacle for hand-carrying said receptacle;
   bin means defined by said first back wall portion, a portion of said pair of vertical sidewalls, a portion of said planar bottom, and a second back wall portion disposed in parallel relation to and apart from said first back wall portion;
   tray means disposed in said bin means for receiving small surgical instruments; and
   shield means positioned adjacent said handle means and said bin means for shielding a holder's hand from contact with said instruments while said instruments are being placed into said receptacle or said tray means.

22. The combination of claim 21 wherein said tray means includes retaining means for securing small surgical instruments on said tray means.

23. The combination of claim 22 wherein said retaining means comprises a magnetic member.

24. The combination of claim 22 wherein said retaining means comprises a plurality of polystyrene strips adaptable to receive sharp ends of said small surgical instruments.

25. The combination of claim 21 wherein said shield means includes a flared shield having a plate portion positioned transverse to a longitudinal axis of said receptacle and extended flanges which project from said plate portion over at least a portion of said handle means to cover at least a portion of said holder's hand when said holder grasps said handle means.

* * * * *